United States Patent [19]

Foster

[11] 4,235,791

[45] Nov. 25, 1980

[54] PROCESS FOR DEHYDROGENATION OF STEROLS TO PRODUCE DELTA 4-3-KETOSTEROIDS

[75] Inventor: Charles H. Foster, Kingsport, Tenn.

[73] Assignee: Eastman Kodak Company, Rochester, N.Y.

[21] Appl. No.: 81,956

[22] Filed: Oct. 4, 1979

[51] Int. Cl.$^3$ .............................................. C07J 9/00
[52] U.S. Cl. ................................. 260/397.2; 260/397.3
[58] Field of Search ......................... 260/397.25, 397.2

[56] References Cited

U.S. PATENT DOCUMENTS

| | | | |
|---|---|---|---|
| 4,072,697 | 2/1978 | Sekine et al. | 260/397.25 |
| 4,148,810 | 4/1979 | Struve | 260/397.25 |

*Primary Examiner*—Elbert L. Roberts
*Attorney, Agent, or Firm*—Clyde L. Tootle; Daniel B. Reece, III

[57] ABSTRACT

This invention relates to the dehydrogenation of a 3-$\beta$-hydroxy steroid or a mixture of soy sterols to form the corresponding mixture of $\Delta^4$-3-keto derivatives of phytosterols, the improvement which comprises dehydrogenating the steroid or mixture of sterols using an activated non-pyrophoric nickel catalyst and carrying out the oxidation in the presence of a diaryl ketone. One such process uses a non-pyrophoric Raney nickel type catalyst and a diaryl ketone, such as benzophenone as a hydrogen acceptor.

16 Claims, No Drawings

PROCESS FOR DEHYDROGENATION OF STEROLS TO PRODUCE DELTA 4-3-KETOSTEROIDS

This invention relates to the dehydrogenation of a 3-β-hydroxy steroid or a mixture of soy sterols to form the corresponding $\Delta^4$-3-keto derivatives of phytosterols using an activated nickel catalyst and in the presence of a diaryl ketone hydrogen acceptor.

The naturally occurring phytosterol components of vegetable oils such as soy oils are composed of mixtures of phytosterols which can be used in the preparation of certain pharmaceuticals such as progesterone which itself also can be used to prepare other steroids, such as cortisone and the like. However, an economical route to the preparation of progesterone from soy sterols involves first the dehydrogenation of such sterols to the $\Delta^4$-3-keto derivatives as the initial step. The 3β-OH of the sterol is dehydrogenated to a ketone with rearrangement of the $\Delta^5$ double bond into conjugation with the ketone. Catalytic dehydrogenation is an economical method for this oxidation-rearrangement process. This catalytic dehydrogenation provides a process for dehydrogenation of $\Delta^5$-sterols to ketones with a simultaneous sift of the $\Delta^5$ double bond to the $\Delta^4$ position in conjugation with the carbonyl group. Raney nickel has been used for this reaction, as disclosed in Chakravarti, Chakravarti, and Metra, Nature, 193, 1071 (1962) or in the presence of a hydrogen acceptor as disclosed in E. C. Kleiderer, and E. C. Kornfeld, J. Org. Chem., 13, 455 (1948) and Kleiderer, Rice, Conquest and Williams, U.S. Dept. of Commerce, Office of the Publication Board, Report PB 981, 1945. It would therefore be an advance in the state of the art to provide an improved process for the catalytic dehydrogenation of soy sterols.

In accordance with the present invention soy sterols can be dehydrogenated to the corresponding 4-en-3-one derivatives using an activated nickel catalyst in the presence of a diaryl ketone hydrogen acceptor.

The activated nickel catalyst can be conventional activated nickel catalyst such as a Raney nickel type catalyst, preferably an activated non-pyrophoric powder such as that supplied by Ventron Corp. The dehydrogenation is carried out in the presence of a diaryl ketone hydrogen acceptor. The amount of diaryl ketone employed in the dehydrogenation is from about 1 mole ketone per mole steroid or soy sterols up to about 3 moles ketone per mole steroid or soy sterols. The rate of the dehydrogenation is reduced as the amount of ketone is increased. In some cases it may be advantageous to carry out the reaction in the presence of a small amount of base (e.g. $K_2CO_3$) in order to minimize dehydration of the sterols at the elevated temperature. The amount of base employed is about 1/30, by weight, based on the weight of steroids or soy sterols. The hydrogen acceptors can be, for example, benzophenone, substituted benzophenones, and the like. The dehydrogenation is preferably carried out at elevated temperatures such as about 150°C. to about 350°C., preferably 200° C.-300° C., most preferably 240°-260° C. At temperatures lower than 150° C., the dehydrogenation reaction is too slow and above 350° C. there is some decomposition of the soy sterols. Use of benzophenone allows the reaction to be carried out at atmospheric pressure in a reasonable reaction rate. The period of time used for the dehydrogenation depends on the temperature used. However, at temperatures of 200° C.-300° C. the reaction is substantially completed after about 8 hours.

The amount of catalyst employed varies with the amount soy sterol used and the speed of reaction desired for the dehydrogenation reaction. Generally, an amount of catalyst used can be equal to about 20 to 40 percent, preferably 25 to 30 percent, based on the weight of the soy sterols to be used. A solvent is not needed which is one of the unique features of the process. However, a solvent can be used if desired.

This invention can be further illustrated by the following examples, although it will be understood that these examples are included merely for purposes of illustration and are not intended to limit the scope of the invention unless otherwise specifically indicated.

EXAMPLE 1

Preparation of $\Delta$4-3-keto derivatives of soy sterols was carried out using 30.0 g of soy sterols (~22% stigmasterol, 78% sitosterol/campesterol), 15 g of benzophenone and 12 g of activated non-pyrophoric nickel catalyst (Ventron). The mixture was heated at 260° for 2 hrs. in a stirred round bottom flask. The mixture was cooled to room temperature. GLC assay of the product showed it to be 85% $\Delta$4-3-ketosteroids. The product was isolated by dissolving in $CH_2Cl_2$, filtering off the catalyst and then stripping off the $Ch_2Cl_2$ and benzophenone/benzohydrol/diphenylmethane under vacuum. The $\Delta$4-3-keto derivatives of soy sterols are then reacted by ozonolysis to form the 4-stigmasten-3-one-derived aldehyde material, 3-ketodinor-4-cholen-22-aldehyde, which can be isolated from the other $\Delta$4-3-keto derivatives of soy sterols by either chromatography or by treatment with sodium bisulfite and extraction with a suitable organic solvent such as toluene.

EXAMPLE 2

Stigmasterol (25.0 g), benzophenone (12.5 g), activated non-pyrophoric nickel catalyst (10 g, Ventron Corp.), and 1.0 g of $K_2CO_3$ were heated at 260° for 2½hrs. GLC assay of the reaction mixture showed at least 82% 4,22-stigmastadien-3-one with only minor amounts of by-products. The mixture was cooled and dissolved in ethyl acetate, filtered and concentrated in vaccuo. Benzophenone and its reduction products were distilled off at 150°-200° (5-10 torr). The residue (25.0 g) was recrystallized from hexane to give 12.5 g of pure 4,22-stigmastadiene-3-one (mp 121°-123°).

EXAMPLE 3

Cholesterol (20 g), benzophenone (12.5 g), activated non-pyrophoric nickel catalyst (10 g, Ventron Corp.), and 1.0 g of $K_2CO_3$ were heated at 260° for 2½hrs. GLC assay of the reaction mixture showed at least 82% 4-cholesten-3-one with only minor amounts of by-products. The mixture was cooled and dissolved in ethyl acetate, filtered and concentrated in vaccuo. Benzophenone and its reduction products were distilled off at 150°-200° C (5-10 torr).

EXAMPLE 4

Sitosterol (25.0 g), benzophenone (12.5 g), activated non-pyrophoric nickel catalyst (10 g, Ventron Corp.), and 1.0 g of $K_2CO_3$ were heated at 260° for 2½hrs. The mixture was cooled and dissolved in ethyl acetate, filtered and concentrated in vaccuo. Benzophenone and its reduction products were distilled off at 150 ®--200° (5-10 torr).

The process of the present invention provides an improved method for the dehydrogenation of steroids and soy sterols to $\Delta^4$-3-ketosteroids. Further, the $\Delta^4$-3-ketosteroids can be used to provide starting materials for preparation of valuable steriods such as the cortical steroids.

The invention has been described in detail with particular reference to preferred embodiments thereof, but it will be understood that variations and modifications can be effected within the spirit and scope of the invention.

I claim:

1. A process which comprises dehydrogenating a 3-$\beta$-hydroxy steroid or mixture of soy sterols to form the corresponding $\Delta^4$-3-keto derivatives, the improvement which comprises dehydrogenating said steroid or mixture of sterols using an activated non-pyrophoric nickel catalyst and in the presence of a diaryl ketone solvent.

2. A process according to claim 1 wherein said 3-$\beta$-hydroxy steroid is stigmasterol.

3. A process according to claim 2 wherein said catalyst is an activated non-pyrophoric nickel catalyst.

4. A process according to claim 3 wherein said diaryl ketone is benzophenone.

5. A process according to claim 2 wherein said catalyst is a non-pyrophoric Raney nickel type catalyst.

6. A process according to claim 5 wherein said diaryl ketone is 3-methyl benzophenone.

7. A process according to claim 1 wherein said 3-$\beta$-hydroxy steroid is cholesterol.

8. A process according to claim 7 wherein said catalyst is an activated non-pyrophoric nickel catalyst.

9. A process according to claim 8 wherein said diaryl ketone is benzophenone.

10. A process according to claim 7 wherein said catalyst is a non-pyrophoric Raney nickel type catalyst.

11. A process according to claim 10 wherein said diaryl ketone is 3-methyl benzophenone.

12. A process according to claim 1 wherein said 3-$\beta$-hydroxy steroid is sitosterol.

13. A process according to claim 12 wherein said catalyst is an activated non-pyrophoric nickel catalyst.

14. A process according to claim 13 wherein said diaryl ketone is benzophenone.

15. A process according to claim 12 wherein said catalyst is a non-pyrophoric Raney nickel type catalyst.

16. A process according to claim 15 wherein said diaryl ketone is 3-methyl benzophenone.

* * * * *